(12) United States Patent
Young et al.

(10) Patent No.: US 7,959,629 B2
(45) Date of Patent: *Jun. 14, 2011

(54) MULTI-ZONE BIPOLAR ABLATION PROBE ASSEMBLY

(75) Inventors: Kimbolt Young, Newtonville, MA (US); Steve Anderson, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 46 days.

This patent is subject to a terminal disclaimer.

(21) Appl. No.: 12/173,653

(22) Filed: Jul. 15, 2008

(65) Prior Publication Data
US 2008/0269739 A1 Oct. 30, 2008

Related U.S. Application Data

(63) Continuation of application No. 10/684,086, filed on Oct. 10, 2003, now Pat. No. 7,416,549.

(51) Int. Cl.
*A61B 18/14* (2006.01)
(52) U.S. Cl. .......................................... 606/41
(58) Field of Classification Search .................. 606/41
See application file for complete search history.

(56) References Cited

U.S. PATENT DOCUMENTS

| | | | |
|---|---|---|---|
| 5,242,441 A | 9/1993 | Avitall | |
| 5,611,803 A | 3/1997 | Heaven et al. | |
| 5,620,481 A * | 4/1997 | Desai et al. | 607/101 |
| 5,672,173 A | 9/1997 | Gough et al. | |
| 5,672,174 A | 9/1997 | Gough et al. | |
| 5,697,909 A | 12/1997 | Eggers et al. | |
| 5,724,988 A | 3/1998 | Dennehey et al. | |
| 5,766,134 A | 6/1998 | Lisak et al. | |
| 5,810,804 A | 9/1998 | Gough et al. | |
| 5,827,276 A | 10/1998 | LeVeen et al. | |
| 5,855,576 A | 1/1999 | LeVeen et al. | |
| 5,863,290 A | 1/1999 | Gough et al. | |
| 5,868,740 A | 2/1999 | LeVeen et al. | |
| 5,913,855 A | 6/1999 | Gough et al. | |
| 5,928,229 A | 7/1999 | Gough et al. | |

(Continued)

FOREIGN PATENT DOCUMENTS

DE 2124684 11/1972

(Continued)

OTHER PUBLICATIONS

PCT International Search Report for PCT/US2004/033084, Applicant: Scimed Life Systems, Inc., Form PCT/ISA/210 and 220, dated Jan. 25, 2005 (8pages).

(Continued)

*Primary Examiner* — Lee S Cohen
(74) *Attorney, Agent, or Firm* — Vista IP Law Group LLP

(57) ABSTRACT

A medical probe assembly, tissue treatment system, and method are provided for ablating tissue. The probe assembly comprises an elongated member and electrode elements mechanically coupled to the distal end of the elongated member. The electrode elements are configurable as two bipolar electrode pairs with a common electrode element. At least one of the electrode elements comprises a plurality of electrodes (such as, e.g., needle electrodes) radially extendable from the elongated member. An ablation source, such as a radio frequency source, can be connected to the probe assembly in order to convey ablation energy to the electrode pairs, either simultaneously or sequentially.

18 Claims, 9 Drawing Sheets

U.S. PATENT DOCUMENTS

| | | |
|---|---|---|
| 5,980,517 A | 11/1999 | Gough |
| 6,022,354 A | 2/2000 | Mercuri et al. |
| 6,071,280 A | 6/2000 | Edwards et al. |
| 6,090,105 A | 7/2000 | Zepeda et al. |
| 6,179,832 B1 | 1/2001 | Jones et al. |
| 6,312,429 B1 | 11/2001 | Burbank et al. |
| 6,379,353 B1 | 4/2002 | Nichols |
| 6,470,218 B1 | 10/2002 | Behl |
| 6,575,967 B1 | 6/2003 | LeVeen et al. |
| 7,416,549 B2 * | 8/2008 | Young et al. ............ 606/41 |
| 2002/0022864 A1 | 2/2002 | Mahvi et al. |
| 2002/0156472 A1 | 10/2002 | Lee et al. |
| 2004/0158239 A1 * | 8/2004 | Behl et al. ............ 606/41 |

FOREIGN PATENT DOCUMENTS

| | | |
|---|---|---|
| WO | WO 98/52480 | 11/1998 |
| WO | WO 99/32041 | 7/1999 |
| WO | WO 02/22032 | 3/2002 |

OTHER PUBLICATIONS

PCT Written Opinion for PCT/US2004/033084, Applicant: Scimed Life Systems, Inc., Form PCT/ISA/237 dated Jan. 25, 2005 (5pages).

LeVeenTM Needle Electrode (brochure) Radio TherapeuticsTM Corporation, 2685 Marine Way, Mountain View, CA 9043.

* cited by examiner

MULTI-ZONE BIPOLAR ABLATION PROBE ASSEMBLY

RELATED APPLICATION

This application is a continuation of U.S. patent application Ser. No. 10/684,086, filed Oct. 10, 2003, now U.S. Pat. No. 7,416,549, the entire disclosure of which is expressly incorporated by reference herein.

FIELD OF THE INVENTION

The field of the invention relates generally to the structure and use of radio frequency (RF) electrosurgical probes for the treatment of tissue, and more particularly, to electrosurgical probes having multiple tissue-penetrating electrodes that are deployed in an array to treat large volumes of tissue.

BACKGROUND OF THE INVENTION

The delivery of radio frequency (RF) energy to target regions within tissue is known for a variety of purposes of particular interest to the present invention. In one particular application, RF energy may be delivered to diseased regions (e.g., tumors) for the purpose of ablating predictable volumes of tissue with minimal patient trauma. RF ablation of tumors is currently performed using one of two core technologies.

The first technology uses a single needle electrode, which when attached to a RF generator, emits RF energy from the exposed, uninsulated portion of the electrode. This energy translates into ion agitation, which is converted into heat and induces cellular death via coagulation necrosis. In theory, RF ablation can be used to precisely sculpt the volume of necrosis to match the extent of the tumor. By varying the power output and the type of electrical waveform, it is theoretically possible to control the extent of heating, and thus, the resulting ablation. The diameter of tissue coagulation from a single electrode, however, is limited by heat dispersion.

The second technology utilizes multiple needle electrodes, which have been designed for the treatment and necrosis of tumors in the liver and other solid tissues. U.S. Pat. No. 6,379,353 discloses such a probe. The ablation probe disclosed in U.S. Pat. No. 6,379,353, referred to as the LeVeen Needle Electrode, comprises a cannula having a needle electrode array, which is reciprocatably mounted within the cannula to alternately deploy the electrode array from the cannula and retract electrode array within the cannula. The individual electrodes within the array have spring memory, so that they assume a radially outward, arcuate configuration as they are deployed from the cannula. In general, a multiple electrode array creates a larger lesion than that created by a single needle electrode.

When creating lesions using needle electrode arrays, RF energy is commonly delivered to the tissue in one of several ways. In the first arrangement illustrated in FIG. 1, RF current may be delivered to an electrode array 10 in a monopolar fashion, which means that current will pass from the electrode array 10 to a dispersive electrode 12 attached externally to the patient, e.g., using a contact pad placed on the patient's flank. In a second arrangement illustrated in FIG. 2, the RF current is delivered to an electrode array 20 in a bipolar fashion, which means that current will pass between "positive" and "negative" electrodes 22 within the array 22. Bipolar arrangements, which require the RF energy to traverse through a relatively small amount of tissue between the tightly spaced electrodes, are more efficient than monopolar arrangements, which require the RF energy to traverse through the thickness of the patient's body. As a result, bipolar electrode arrays generally create larger and/or more efficient lesions than monopolar electrode arrays. To provide even larger lesions, it is known to operate two electrode arrays in a bipolar arrangement. For example, FIG. 3 illustrates two electrode arrays 30 and 32 that are configured to emit RF energy between each other. Specifically, the first electrode array 30 is operated as an active electrode array that emits RF energy, and the second electrode array 32 is operated as a return electrode array that receives the RF energy, thereby ablating the tissue between the electrode arrays 30 and 32.

Physician feedback has indicated that there is a continuing need for treating larger tissue volume. For the electrode configuration illustrated in FIG. 3, the distance between the two electrode arrays affects the volume of tissue ablated. For example, if the distance between the electrode arrays were to be lengthened to try to ablate a longer tissue volume, the energy transmitted between the electrode arrays may thin and not fully ablate the intermediate tissue. As a result, an hourglass shaped ablation, rather than the desired uniform circular/elliptical ablation, would be created.

As a consequence, when ablating lesions that are larger than the capability of the above-mentioned devices, the common practice is to stack ablations (i.e., perform multiple ablations) within a given area. This requires multiple electrode placements and ablations facilitated by the use of ultrasound imaging to visualize the electrode in relation to the target tissue. Because of the echogenic cloud created by the ablated tissue, however, this process often becomes difficult to accurately perform. This considerably increases treatment duration and requires significant skill for meticulous precision of multiple electrode placement.

SUMMARY OF THE INVENTION

In accordance with a first aspect of the present invention, a medical probe assembly for ablating tissue is provided. The probe assembly comprises an elongated member, which in the preferred embodiment, is rigid to allow for percutaneous or laparoscopic introduction into a patient's body. The probe assembly further comprises electrode elements mechanically coupled to the distal end of the elongated member. The electrode elements are configurable as two bipolar electrode pairs, wherein the other electrode element is common to the bipolar electrode pairs. In this manner, the electrode elements are configured in a unique bipolar arrangement that is capable of efficiently ablating tissue. The electrode elements can be variously configured to form the bipolar electrode pairs. For example, two of the electrode elements can be active elements, and the other electrode element a return element. Or, the two electrode elements can be return elements, and the other electrode element an active element. The electrode elements can be statically configured (i.e., any given electrode element has a dedicated functionality, either an active element or a return element, but not both) or dynamically configured (i.e., any given electrode element can be either an active element or a return element during any given time).

In a preferred embodiment, the electrode elements are mounted to the elongated member in an axial arrangement to allow efficient ablation of tissue along its thickness. At least one of the electrode elements comprises a plurality of electrodes (such as, e.g., needle electrodes) radially extendable from the elongated member. Although the present invention should not be so limited in its broadest aspects, the radially extendable electrodes allows the probe assembly to generate a three-dimensional lesion (i.e., a lesion that linearly extends along the length of the elongated member and radially extends from the elongated member). Each of the other electrode elements can optionally comprise a plurality of electrodes that radially extend from the elongated member in order to provide additional three-dimensionality to the lesion. Alternatively, one or more of the electrodes may comprise other types of electrode(s), such as ring electrodes. Optionally, additional electrode(s), which may also be radially deployable from the elongated member, can be mechanically coupled to the distal end of the elongated member. In this manner, a longer three-dimensional lesion can be created.

In accordance with a second aspect of the present invention, another medical probe assembly for ablating tissue is provided. The probe assembly comprises an elongated member, which in the preferred embodiment, is rigid to allow for percutaneous or laparoscopic introduction into a patient's body. The probe assembly further comprises electrode arrays mechanically coupled to the distal end of the member. Each of the electrode arrays comprises a plurality of needle electrodes. The electrode arrays are configurable as two bipolar electrode pairs, wherein the other electrode array is common to the bipolar electrode pairs. In this manner, the electrode arrays are configured in a unique bipolar arrangement that is capable of efficiently ablating tissue. The electrode arrays can be variously configured to form the bipolar electrode pairs in the same manner previously described with respect to the electrode elements. Although the present invention should not be so limited in its broadest aspects, the electrode arrays allow the probe assembly to generate a three-dimensional lesion. In a preferred embodiment, the electrode arrays are mounted to the elongated member in an axial arrangement to allow efficient ablation of tissue along the thickness of the tissue. Optionally, additional electrode arrays may be mechanically coupled to the distal end of the elongated member to provide a longer lesion along the thickness of the tissue.

The electrode arrays may be optionally deployable from the elongated member. When deployed, the electrode arrays may assume various geometries. For example, the active electrode arrays may assume an outwardly curved shape when deployed. The active electrode arrays may further assume an everted shape. For example, both active electrode arrays can assume a proximally everted shape. Or a proximal active electrode array can assume a distally everted shape, and a distal active electrode array can assume a proximally everted shape. The return electrode array may assume an outwardly straight shape.

The electrode arrays may be deployed in a variety of manners. For example, the elongated member may comprise an inner shaft and a cannula having a lumen in which the inner shaft is reciprocatably disposed. In this case, the electrode arrays may be mounted to the inner shaft, and can be alternately deployed from and housed within the cannula lumen. Alternatively, the cannula can be an inner cannula, in which case, the probe assembly can further comprise an outer cannula having a lumen in which the inner cannula is reciprocatably disposed. Instead of being mounted to the inner shaft, one of the two electrode arrays may be mounted to the inner cannula and can be alternately deployed from and housed within the outer cannula lumen. This latter deployment technique is especially useful if the active electrode arrays are to be deployed in opposite directions.

In accordance with a third aspect of the present invention, a tissue ablation system is provided. The tissue ablation system comprises a medical probe assembly, such as one of those previously described. The tissue ablation system further comprises an ablation source (such as, e.g., a radio frequency ablation source) electrically coupled to the two electrode elements and the other electrode element, such that ablation energy can be delivered between the electrode elements. The tissue ablation system further comprises a controller for configuring the electrode elements in bipolar electrode pairs in the manner previously described. The controller is configured for causing the ablation source to simultaneously or sequentially convey ablation energy to the bipolar electrode pairs.

In accordance with a fourth aspect of the present inventions, a method of treating tissue having a diseased region (e.g., a tumor) is provided. The method comprises placing two electrode elements in contact with the diseased region, and placing another electrode elements in contact with the diseased region in an axial arrangement with the two electrode elements, wherein the other electrode element is between the two electrode elements. The electrode elements may be on a single device, or distributed among at least two separate devices. The method further comprises conveying ablation energy between the two electrode elements and the other element to create two lesions within the diseased region, wherein the two lesions, in composite, form a three-dimensional lesion. The ablation energy can either be conveyed from the two electrode elements to the other electrode element, or from the other electrode element to the two electrode elements. The electrode elements may be mounted on a single ablation probe or on two or more ablation probes.

Thus, it can be appreciated that the distance that the ablation energy must travel between electrode elements is half that of the spacing between the two electrode elements. As a result, a more efficient ablation process is achieved. If the diseased region has a thickness, the two electrode elements and other electrode element can be distributed along the thickness of the diseased region, in which case, the three-dimensional lesion can be advantageously created through the thickness of the diseased region without moving the two electrode elements and other electrode element.

The method may optionally comprise placing an additional electrode element in contact with the tissue, and conveying ablation energy between the additional electrode element and one of the two electrode elements. In this manner, longer three-dimensional lesions may be created and/or the distance over which the ablation energy travels may be further reduced. In any event, the ablation energy may be simultaneously conveyed between the two electrode elements and the other electrode element in order to simultaneously create the two lesions, or the ablation energy may be sequentially conveyed between the two electrode elements and the other electrode element in order to sequentially create the two lesions. In either case, the two lesions compositely form the three-dimensional lesion.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 4:
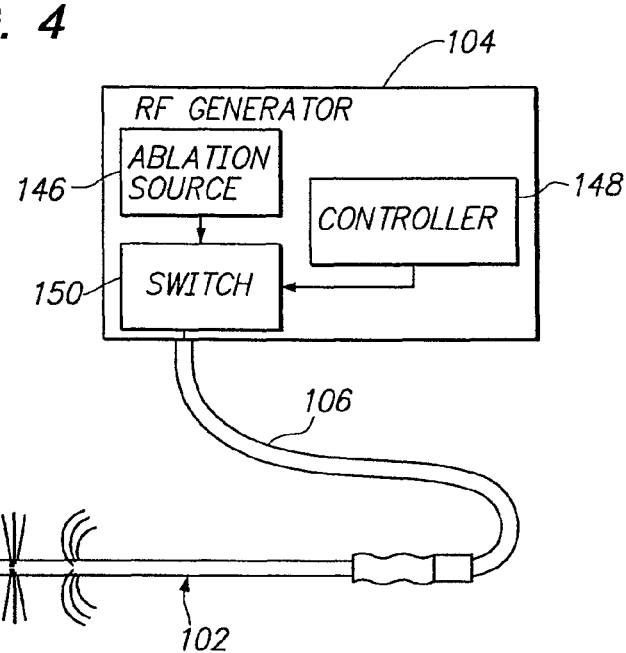
FIG. 4 is a plan view of a tissue ablation system constructed in accordance with one preferred embodiment of the present invention.

FIG. 4 illustrates a tissue ablation system 100 constructed in accordance with a preferred embodiment of the present invention. The tissue ablation system 100 generally comprises a probe assembly 102 configured for introduction into the body of a patient for ablative treatment of target tissue, a radio frequency (RF) generator 104 configured for supplying RF energy to the probe assembly 102 in a controlled manner, and a cable 106 electrically connecting the probe assembly 102 to the RF generator 104.

Figure 5:
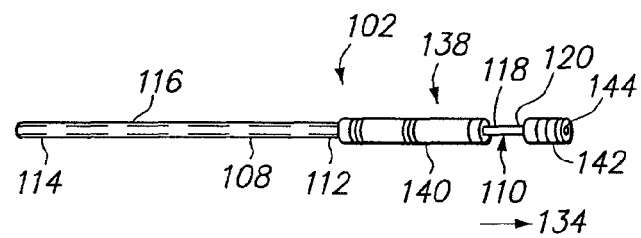
FIG. 5 is a perspective view of a preferred ablation probe assembly used in the tissue treatment system of FIG. 1, wherein the probe assembly is particularly shown in its retracted state.
Figure 6:
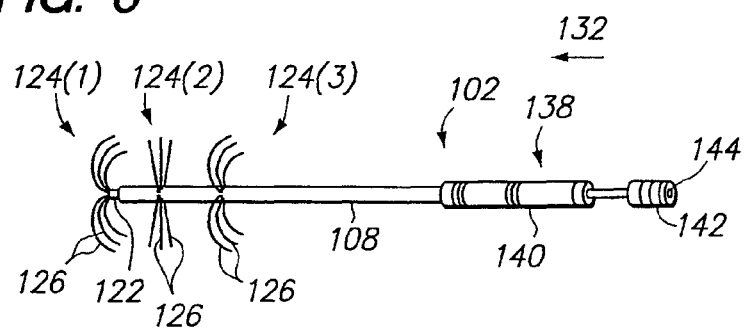
FIG. 6 is a perspective view of the probe assembly of FIG. 5, wherein the probe assembly is particularly shown in its deployed state.

Referring specifically now to FIGS. 5 and 6, the probe assembly 102 generally comprises an elongated cannula 108 and an inner probe 110 slidably disposed within the cannula 108. The cannula 108 has a proximal end 112, a distal end 114, and a central lumen 116 (shown in phantom in FIG. 5) extending through the cannula 108. As will be described in further detail below, the cannula 108 may be rigid, semi-rigid, or flexible depending upon the designed means for introducing the cannula 108 to the target tissue. The cannula 108 is composed of a suitable material, such as plastic, metal or the like, and has a suitable length, typically in the range from 5 cm to 30 cm, preferably from 10 cm to 20 cm. If composed of an electrically conductive material, the cannula 108 is preferably covered with an insulative material. The cannula 108 has an outside diameter consistent with its intended use, typically being from 1 mm to 5 mm, usually from 1.3 mm to 4 mm. The cannula 108 has an inner diameter in the range from 0.7 mm to 4 mm, preferably from 1 mm to 3.5 mm.

The inner probe 110 comprises a reciprocating shaft 118 having a proximal end 120 (shown in FIG. 5) and a distal end 122 (shown in FIG. 6), and three axially aligned electrode arrays 124 (shown in FIG. 6), each of which comprises a plurality of tissue penetrating needle electrodes 126 suitably mounted to the distal end 122 of the inner probe shaft 118. The three electrode arrays 124 are configured into two bipolar electrode pairs, with the electrode array 124(2) being common to the electrode pairs. That is, a first electrode pair is formed by the electrode arrays 124(1) and 124(2), and a second electrode pair is formed by the electrode arrays 124(3) and 124(2). The electrode array 124(2) has a polarization that is opposite to the polarization of the electrode arrays 124(1) and 124(3). In the illustrated embodiment, the electrode arrays 124(1) and 124(3) are configured as distal and proximal active arrays (i.e., electrode arrays from which ablation energy is conveyed), respectively, and the electrode array 124(2) is configured as a return array (i.e., electrode array to which ablation energy is conveyed).

Figure 7:
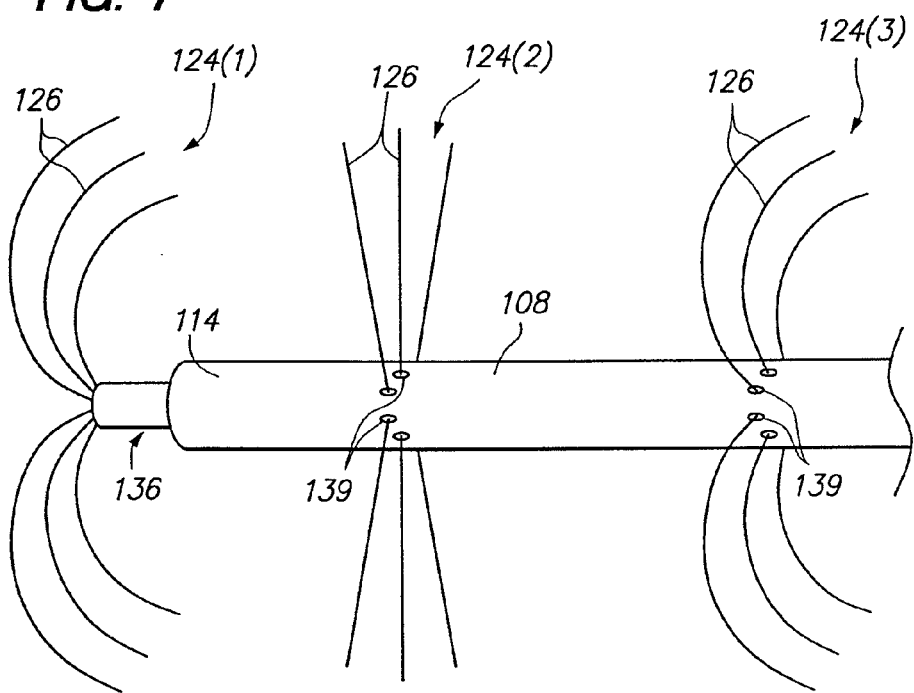
FIG. 7 is a close up view of the distal end of the deployed probe assembly of FIG. 6.
Figure 8:
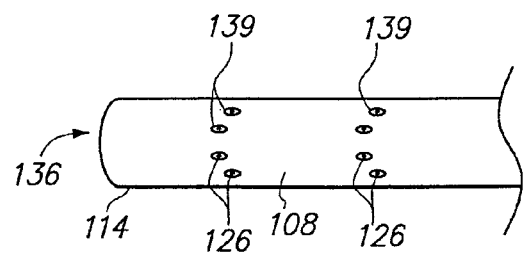
FIG. 8 is a close up view of the distal end of the retracted probe assembly of FIG. 5.

Like the cannula 108, the inner probe shaft 118 is composed of a suitable material, such as plastic, metal or the like. It can be appreciated that longitudinal translation of the inner probe shaft 118 relative to the cannula 108 in a distal direction 132 deploys the electrode arrays 124 from the distal end 114 of the cannula 108 (FIG. 6), and longitudinal translation of the inner probe shaft 118 relative to the cannula 108 in a proximal direction 134 retracts the electrode arrays 124 into the distal end 114 of the cannula 108 (FIG. 5). As best seen in FIGS. 7 and 8, the cannula 108 comprises a distal opening 136 in which the cannula lumen 116 terminates, and circumferentially disposed ports 139 that extend through the wall of the cannula 108. The needle electrodes 126 of the distal active array 124(1) deploy out from the distal opening 136, and the needle electrodes 126 of the return array 124(2) and the proximal active array 124(3) deploy out from the ports 139. Preferably, the ports 139 are somewhat elongated and extend in the distal direction in order to facilitate deployment of the needle electrodes 126 when the probe shaft 118 is distally displaced. As illustrated in FIG. 8, the distal ends of the needle electrodes 126, when retracted, reside within the ports 139 in order to facilitate movement of the needle electrodes 126 from the ports 139 during deployment.

Each of the individual needle electrodes 126 takes the form of a small diameter metal element, which can penetrate into tissue as it is advanced from a target site within the target region. The needle electrodes 126 are resilient and pre-shaped to assume a desired configuration when advanced into tissue. When deployed from the cannula 108 (FIG. 7), each of the active electrode arrays 124(1) and 124(3) is placed in a three-dimensional configuration that defines a generally ellipsoidal or spherical volume having a periphery with a maximum radius in the range from 0.5 to 3 cm. The needle electrodes 126 of the active arrays 124(1) and 124(3) are curved and diverge radially outwardly from the cannula 108 in a uniform pattern, i.e., with the spacing between adjacent needle electrodes 126 diverging in a substantially uniform and/or symmetric pattern. In the illustrated embodiment, the needle electrodes 126 of the active arrays 124(1) and 124(3) also evert proximally, so that they face partially or fully in the proximal direction 134 when fully deployed. When deployed from the cannula 108, the return electrode array 124(2) is placed in a planar configuration that is generally orthogonal to the axis of the inner probe shaft 118. The needle electrodes 126 of the return array 124(2) are straight and extend radially outward from the cannula 108.

In exemplary embodiments, for any of the electrode arrays 124, pairs of adjacent needle electrodes 126 can be spaced from each other in similar or identical, repeated patterns and can be symmetrically positioned about an axis of the inner probe shaft 118. It will be appreciated that a wide variety of particular patterns can be provided to uniformly cover the region to be treated. It should be noted that a total of six needle electrodes 126 for each array 124 are illustrated in FIG. 4. Additional needle electrodes 126 can be added in the spaces between the illustrated electrodes 126, with the maximum number of needle electrodes 126 determined by the electrode width and total circumferential distance available (i.e., the needle electrodes 126 could be tightly packed).

Each individual needle electrode 126 is preferably composed of a single wire that is formed from resilient conductive metals having a suitable shape memory, such as stainless steel, nickel-titanium alloys, nickel-chromium alloys, spring steel alloys, and the like. The wires may have circular or non-circular cross-sections, but preferably have rectilinear cross-sections. In this manner, the needle electrodes 126 are generally stiffer in the transverse direction and more flexible in the radial direction. By increasing transverse stiffness, proper circumferential alignment of the needle electrodes 126 within the cannula 108 is enhanced. Exemplary needle electrodes will have a width (in the circumferential direction) in the range from 0.2 mm to 0.6 mm, preferably from 0.35 mm to 0.40 mm, and a thickness (in the radial direction) in the range from 0.05 mm to 0.3 mm, preferably from 0.1 mm to 0.2 mm. The distal ends of the needle electrodes 126 may be honed or sharpened to facilitate their ability to penetrate tissue. The distal ends of these needle electrodes 126 may be hardened using conventional heat treatment or other metallurgical processes.

The probe assembly 102 further comprises a connector assembly 138, which includes a connector sleeve 140 mounted to the proximal end 112 of the cannula 108 and a connector member 142 slidably engaged with the sleeve 140 and mounted to the proximal end 120 of the probe shaft 118. The connector member 142 also comprises an electrical connector 144 to which the probe shaft 118 is electrically coupled. The connector assembly 138 can be composed of any suitable rigid material, such as, e.g., metal, plastic, or the like.

Further details regarding the general structure of needle electrode array-type probe arrangements are disclosed in U.S. Pat. No. 6,379,353, which is hereby expressly incorporated herein by reference.

RF current is delivered to the electrode arrays 124 in a bipolar fashion. In particular, RF current will be conveyed from the active electrode arrays 124(1) and 124(3) to the return electrode array 124(2). Because the RF energy need only travel a distance equal to one-half the spacing between the active electrode arrays 124(1) and 124(3) (i.e., between the distal active electrode array 124(1) and the return electrode array 124(2), and between the proximal active electrode array 124(3) and the return electrode array 124(2)), a more efficient ablation process can be performed, as will be described in further detail below.

In order to oppositely polarize the return electrode array 124(2) and the active electrode arrays 124(1) and 124(3), the active electrode arrays 124(1) and 124(3) must be electrically isolated from the return electrode array 124(2) through the probe assembly 102. This can be accomplished in a variety of manners.

For example, insulated RF wires can be routed through the inner probe shaft 118 between the needle electrodes 126 of the respective arrays 124 and the electrical connector 144. In this case, the inner probe shaft 118 and the cannula 108 are preferably composed of an electrically non-conductive material, so that the needle electrodes 126 of the active arrays 124(1) and 124(3) remain electrically isolated from the needle electrodes 126 of the return array 124(3), notwithstanding that the needle electrodes 126 of the arrays 124 are in contact with the inner probe shaft 118 and cannula 108. Alternatively, the inner probe shaft 118 and/or cannula 108 may be composed of an electrically conductive material, such as stainless steel, in which case, the portions of the needle electrodes 126 that are in contact with the inner probe shaft 118 and/or cannula 108 can be coated with an electrically insulative material. If the cannula 108 is electrically conductive, the outer surface of the cannula 108 is also preferably coated within an electrically insulative material. Alternatively, rather than using intermediate conductors, the proximal ends of the needle electrodes 126 may be directly coupled to the connector 144, in which case, the portions of the needle electrodes 126 extending through the inner probe shaft 118 are coated with an electrically insulative material.

Alternatively, the electrically conductive shaft 118 may serve as an intermediate conductor between the active arrays 124(1) and 124(3) and the electrical connector 144, or the return array 124(2) and the electrical connector 144, but not both. In this case, the needle electrodes 126 of the active arrays 124(1) and 124(3) may be in electrical contact with the inner probe shaft 118, while the needle electrodes 126 of the return array 124(2) may be electrically isolated from the inner probe shaft 118 using an insulative coating. Or the needle electrodes 126 of the return array 124(2) may be in electrical contact with the inner probe shaft 118, while the needle electrodes 126 of the active arrays 124(1) and 124(3) may be electrically isolated from the inner probe shaft 118 using an insulative coating. In some cases, as will be described in further detail below, it may be desirable to also electrically isolate the active arrays 124(1) and 124(3) from each other. In this case, only one of the arrays 124(1) and 124(3) should be in electrical contact with the inner probe shaft 118.

Figure 1:
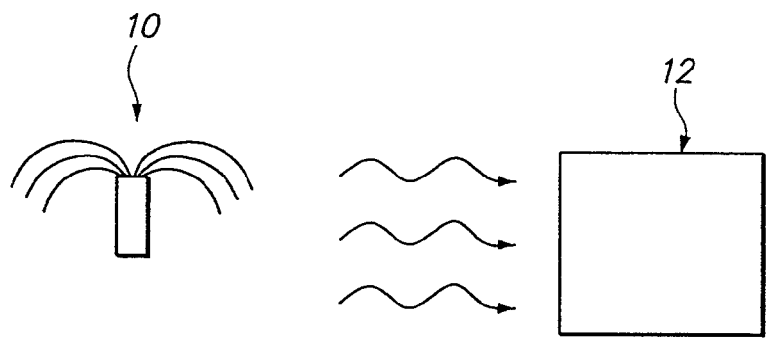
FIG. 1 is a plan view of a prior art monopolar electrode arrangement between an electrode array and an external patch.
Figure 2:
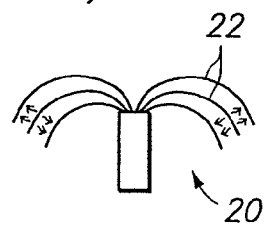
FIG. 2 is a plan view of a prior art bipolar electrode arrangement between needle electrodes on an electrode array.
Figure 3:
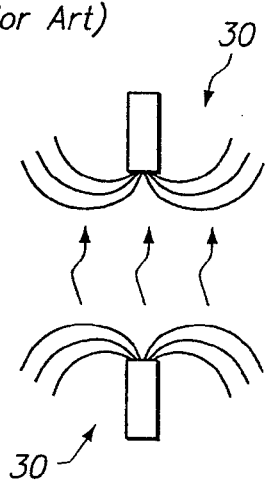
FIG. 3 is a plan view of a prior art bipolar electrode arrangement between two needle electrode arrays.

Referring back to FIG. 1, the RF generator 104 is electrically connected to the electrical connector 144 of the connector assembly 138, which as previously described, is directly or indirectly electrically coupled to the electrode arrays 124. The RF generator 104 is a conventional RF power supply that operates at a frequency in the range from 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000™ (100 W) and RF300™ (200 W). As previously mentioned, the RF generator 104 operates the electrode arrays 124 in a bipolar fashion.

In the illustrated embodiment, the RF generator 104 comprises a RF ablation source 146, a controller 148, and a switch 150. As will be described in further detail below, the controller 148 is configured to control the switch 148 in order to simultaneously or sequentially provide RF energy from the ablation source 146 to the active electrode arrays 124(1) and 124(3), resulting in the desired lesion.

Having described the structure of the tissue ablation system 100, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm$^3$ to 150 cm$^3$, and often from 2 cm$^3$ to 35 cm$^3$. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 9A:
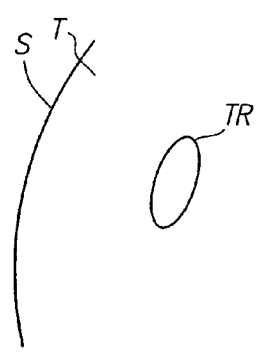
FIGS. 9A-9D are cross-sectional views of one preferred method of using the tissue ablation system of FIG. 4 to treat tissue.
Figure 9B:
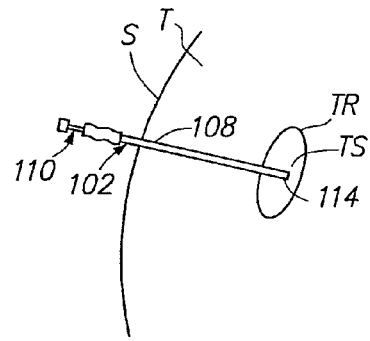

Referring now to FIGS. 9A-9D, the operation of the tissue ablation system 100 is described in treating a treatment region TR within tissue T located beneath the skin or an organ surface S of a patient. The tissue T prior to treatment is shown in FIG. 9A. The probe assembly 102 is first introduced within the treatment region TR, so that the distal end 114 of the cannula 108 is located at the target site TS, as shown in FIG. 9B. This can be accomplished using any one of a variety of techniques. In some cases, the probe assembly 102 may be introduced to the target site TS percutaneously directly through the patient's skin or through an open surgical incision. In this case, the cannula 108 may have a sharpened tip, e.g., in the form of a needle, to facilitate introduction to the treatment region TR. In such cases, it is desirable that the cannula 108 or needle be sufficiently rigid, i.e., have a sufficient column strength, so that it can be accurately advanced through tissue T. In other cases, the cannula 108 may be introduced using an internal stylet that is subsequently exchanged for the inner probe 110. In this latter case, the cannula 108 can be relatively flexible, since the initial column strength will be provided by the stylet. More alternatively, a component or element may be provided for introducing the cannula 108 to the target site TS. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 108 and inner probe 110 can then be introduced through the sheath lumen, so that the distal end 114 of the cannula 108 advances from the sheath into the target site TS.

Figure 9C:
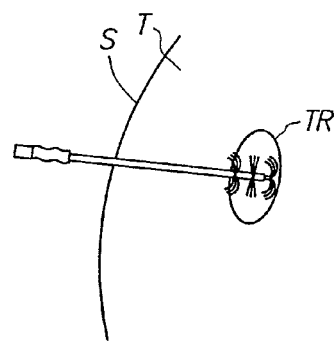
Figure 9D:
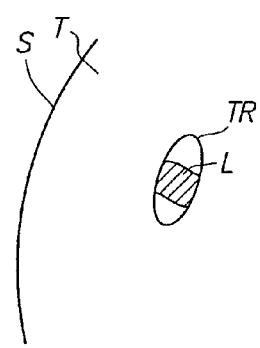

After the cannula 108 is properly placed, the inner probe shaft 118 is distally advanced to deploy the electrode arrays 124 radially outward from the distal end 114 of the cannula 108, as shown in FIG. 9C. Preferably, the electrode arrays 124 are axially disposed along the entire thickness of the treatment region TR. The RF generator 104 is then connected to the connector assembly 138 via the electrical connector 144 and then operated to create a three-dimensional lesion L within the treatment region TR, as illustrated in FIG. 9D.

Figure 10A:
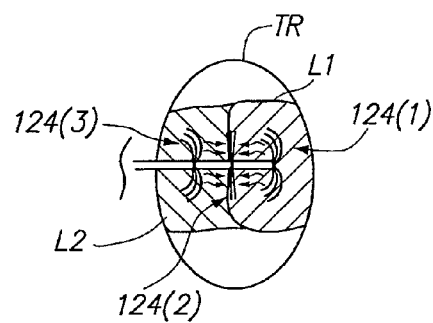
FIGS. 10A-10C are cross-sectional views of two different bipolar arrangements of the probe assembly of FIGS. 5 and 6, particularly showing the use of distal and proximal active electrode arrays and a medial return electrode array.

In particular, the RF generator 104 is configured to simultaneously convey RF energy from the active electrode arrays 124(1) and 124(3) to the return electrode array 124(2). This can be accomplished by the controller 148, which operates the switch 150 to couple the ablation source 146 to the active arrays 124(1) and 124(3), while the return array 124(2) is grounded. Thus, RF energy is conveyed from the distal active array 124(1), through the tissue, to the return array 124(2) to create a first lesion portion L1, and from the proximal active array 124(3), through the tissue, to the return array 124(2) to create a second lesion portion L2 (FIG. 10A). The composite of the lesion portions L1 and L2 forms the lesion L.

Figure 10B:
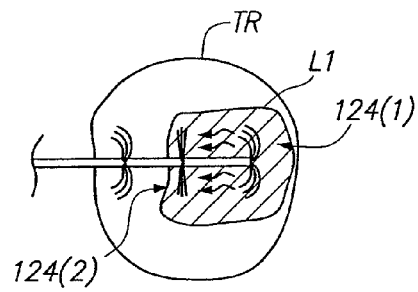
Figure 10C:
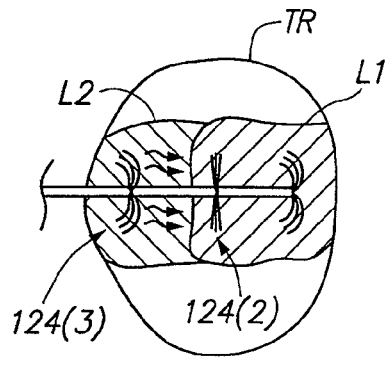

Alternatively, the RF generator 104 may be configured to sequentially convey RF energy from the active electrode arrays 124(1) and 124(3) to the return electrode array 124(2). In particular, with the return array 124(2) grounded, the controller 148 operates the switch 150 to first couple the ablation source 146 to the distal active array 124(1) and decouple the ablation source 146 from the proximal active array 124(3), while conveying RF energy from the ablation source 146. In this manner, RF energy is conveyed to the distal active array 124(1), which in turn, is transmitted through the tissue to the return array 124(2) to create a first lesion portion L1, as illustrated in FIG. 10B. The controller 148 may then operate the switch 150 to decouple the ablation source 146 from the distal active array 124(1) and couple the ablation source 146 to the proximal active array 124(3), while continuing to convey RF energy from the ablation source 146. In this manner, RF energy is then conveyed to the proximal active array 124(3), which in turn, is transmitted through the tissue to the return array 124(2) to create a second lesion portion L2, as illustrated in FIG. 10C.

Thus, it can be appreciated that the treatment system 100 may create multiple bipolar ablation zones (in this case, two) through the thickness of the treatment region TR. Because there are two ablation zones, the ablation process is made more efficient, since the tissue distance between any pair of electrodes is reduced by one-half. This, in combination, with the axial arrangement of the electrode arrays 124 may obviate the need to perform stacked ablations through the thickness of the treatment region TR. In addition, because the electrode arrays 124 radially extend outward, a three-dimensional lesion is created, in contrast to a linear lesion that is typically created using electrode elements that do not extend radially outward, such as ring electrodes. As a result, only one ablation procedure may be needed to ablate the entire treatment region TR (i.e., without repositioning the ablation probe between ablations), or at the least, the number of ablation procedures required to do so will be minimized.

It should be noted that although the electrode arrays 124 were previously described as being configured in a bipolar arrangement by conveying RF current from the electrode arrays 124(1) and 124(3) to the electrode array 124(2), the electrode arrays 124 may be configured in a bipolar arrangement by conveying RF current from the electrode array 124 (2) to the electrode arrays 124(1) and (3). In this case, the electrode arrays 124(1) and 124(3) will serve as distal and proximal return arrays, and the electrode array 124(2) will serve as an active array.

Figure 11A:
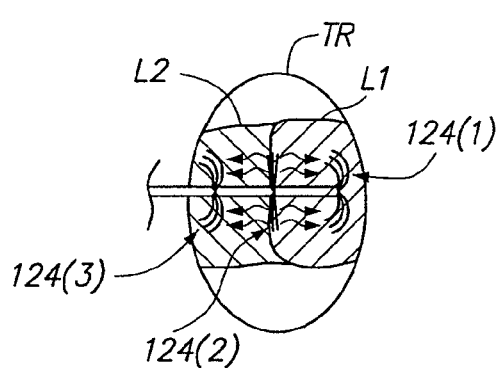
FIGS. 11A-11C are cross-sectional views of two different bipolar arrangements of the probe assembly of FIGS. 5 and 6, particularly showing the use of a medial active electrode array and distal and proximal return electrode arrays.

For example, the RF generator 104 may be configured to simultaneously convey RF energy from the active electrode array 124(2) to the return electrode arrays 124(1) and 124(3). This can be accomplished by the controller 148, which can operate the switch 150 to couple the ablation source 146 to the active array 124(2), while the return arrays 124(1) and 124(2) are grounded. Thus, RF energy is conveyed from the active array 124(2), through the tissue, to the distal return array 124(1) to create a first lesion portion L1, and from the active array 124(2), through the tissue, to the proximal return array 124(3) to create a second lesion portion L2 (FIG. 11A). The composite of the lesion portions L1 and L2 forms the lesion L.

Figure 11B:
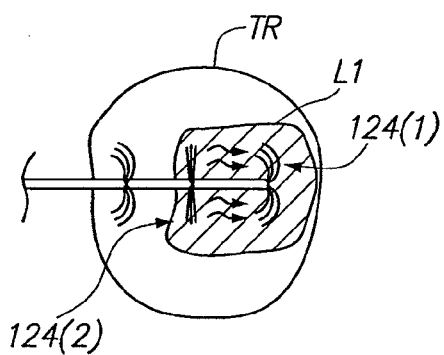
Figure 11C:
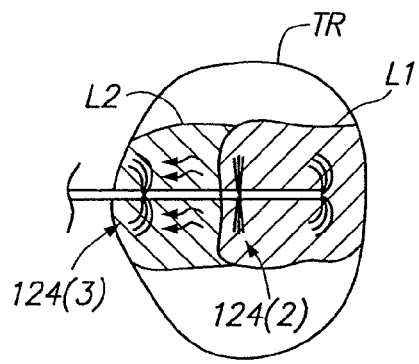

Alternatively, the RF generator 104 may be configured to sequentially convey RF energy from the active electrode array 124(2) to the return electrode arrays 124(1) and 124(3). In particular, with the ablation source 146 coupled to the active array 124(2), the controller 148 may operate the switch 150 to ground the distal return array 124(1) and unground the proximal return array 124(3), while conveying RF energy from the ablation source 146. In this manner, RF energy is conveyed to the active array 124(2), which in turn, is transmitted through the tissue to the distal return array 124(1) to create a first lesion portion L1, as illustrated in FIG. 11B. The controller may then unground the distal return array 124(1) and ground the proximal return array 124(3), while continuing to convey RF energy from the ablation source 146. In this manner, RF energy continues to be conveyed to the active array 124(2), which in turn, is transmitted through the tissue to the proximal return array 124(3) to create a second lesion portion L2, as illustrated in FIG. 11C.

Regardless of which manner the electrode arrays 124 are placed in a bipolar arrangement, ablation probe assemblies constructed in accordance with the present invention can also generate more than two ablation zones. For example, with reference to FIG. 12, a probe assembly 202 that generates four ablation zones will now be described. The probe assembly 202 is similar to the previously described probe assembly 202, with the exception that it comprises an inner probe 210 that carries five axially arranged electrode arrays 224(1)-224 (5) that are configured to form four bipolar electrode pairs. The electrode arrays 224(2) and 224(4) have a polarization that is opposite to the polarization of the electrode arrays 224(1), 224(3), and 224(5). In the illustrated embodiment, the electrode arrays 224(1), 224(3), and 224(5) are configured as distal, medial, and proximal active arrays, respectively, and the electrode arrays 224(2) and 224(4) are configured as distal and proximal return arrays, respectively. Thus, it can be appreciated that the electrode array 224(2) is common to a first bipolar electrode pair formed by electrode arrays 224(1) and 224(2) and a second bipolar electrode pair formed by electrode arrays 224(3) and 224(2). The electrode array 224 (3) is common to the second bipolar electrode pair and a third bipolar electrode pair formed by electrode arrays 224(4) and 224(3). The electrode array 224(4) is common to the third bipolar electrode pair and a fourth bipolar electrode pair formed by electrode arrays 224(5) and 224(4).

Figure 12:
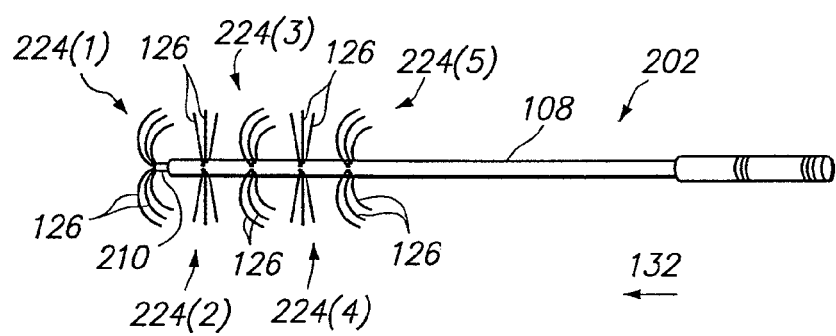
FIG. 12 is a perspective view of another ablation probe assembly that can alternatively be used in the tissue treatment system of FIG. 1, wherein the probe assembly is particularly shown in its deployed state.

As illustrated in FIG. 12, longitudinal translation of the inner probe shaft (not shown) relative to the cannula 108 in the distal direction 132 deploys the electrode arrays 224 from the distal end 114 of the cannula 108. The needle electrodes 126 of the distal active electrode array 224(1) deploy out from the distal opening (not shown) within the inner probe shaft 118, and the needle electrodes 126 of the remaining electrode arrays 224(2)-224(5) deploy out from distal openings (not shown) formed through the wall of the cannula 108.

As with the previously described electrode arrays 124, RF current is delivered to the electrode arrays 224 in a bipolar fashion. In particular, RF current will be conveyed from the active electrode arrays 224(1), 224(3), and 224(5) to the return electrode array 224(2) and 224(4). Because the RF energy need only travel a distance equal to one-quarter the spacing between the active electrode arrays 124(1) and 124 (5) (i.e., between the distal active electrode array 224(1) and the distal return electrode array 224(2), between the medial active electrode array 224(3) and the distal return electrode array 224(2), between the medial active electrode array 224 (3) and the proximal return electrode array 224(4), and between the proximal active electrode array 224(5) and the proximal return electrode array 224(4)), a more efficient ablation process can be performed.

In order to oppositely polarize the active electrode arrays 224(1), 224(3), and 224(5) and the return electrode arrays 224(2) and 224(4), the active electrode arrays 224(1), 224(3), and 224(5) must be electrically isolated from the return electrode arrays 224(2) and 224(4). This can be accomplished in the same manner that the electrode arrays 124(1) and 124(3) and the electrode array 124(2) are electrically isolated, as previously described above.

Figure 13A:
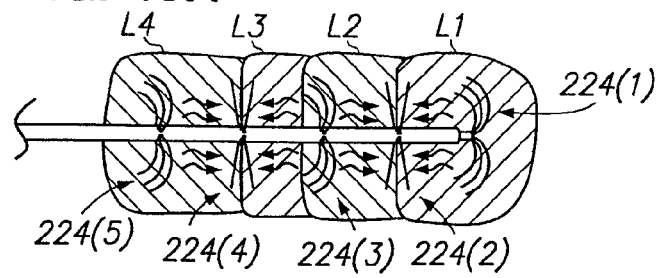
FIGS. 13A-13E are cross-sectional views of two bipolar different arrangements of the probe assembly of FIG. 12, particularly showing the use of distal, medial, and proximal active electrode arrays and distal and proximal return electrode arrays.

Using the probe assembly 202, instead of the probe assembly 102, the system 100 can be operated in the same manner as previously described, with the exception that three active electrode arrays and two return electrode arrays will be configured in a bipolar arrangement. In general, long lesions can be created by the probe assembly 202. In particular, the RF generator 104 is configured to simultaneously convey RF energy from the active electrode arrays 224(1), 224(3), and 224(5) to the return electrode arrays 224(2) and 224(4). This can be accomplished by the controller 148, which can operate the switch 150 to couple the ablation source 146 to the active arrays 124(1), 124(3), and 124(5), while the return arrays 124(2) and 124(4) are grounded. Thus, RF energy is conveyed from the distal active array 224(1), through the tissue, to the distal return array 224(2) to create a first lesion portion L1, from the medial active array 224(3), through the tissue, to the distal return array 224(2) to create a second lesion portion L2, from the medial active array 224(3), through the tissue, to the proximal return array 224(4) to create a third lesion portion L3, and from the proximal active array 224(5), through the tissue, to the proximal return array 224(4) to create a fourth lesion portion L4 (FIG. 13A). The composite of the lesion portions L1-L4 forms the lesion L.

Figure 13B:
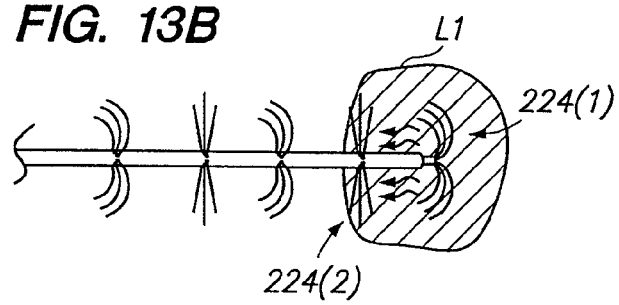

Alternatively, the RF generator 104 may be configured to sequentially convey RF energy from the active electrode arrays 224(1), 224(3), and 224(5) to the return electrode arrays 224(2) and 224(4). In particular, with the ablation source 146 decoupled from the medial and proximal active arrays 224(3) and 224(5), and the proximal return array 224(4) grounded, the controller 148 may first operate the switch 150 to first couple the ablation source 150 to the distal active array 224(1), while conveying RF energy from the ablation source 150. In this manner, RF energy is conveyed to the distal active array 224(1), which in turn, is transmitted through the tissue to the distal return array 224(2) to create a first lesion portion L1, as illustrated in FIG. 13B.

Figure 13C:
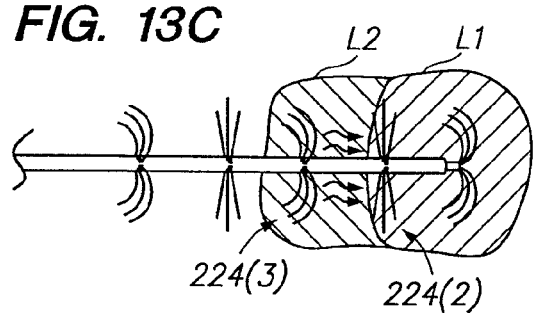
Figure 13D:
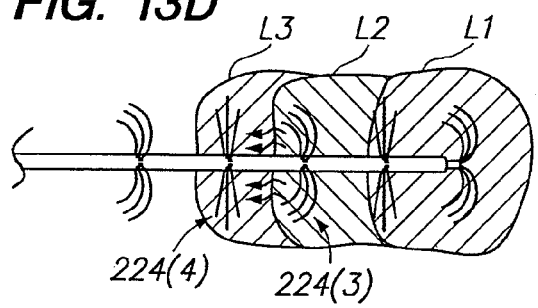
Figure 13E:
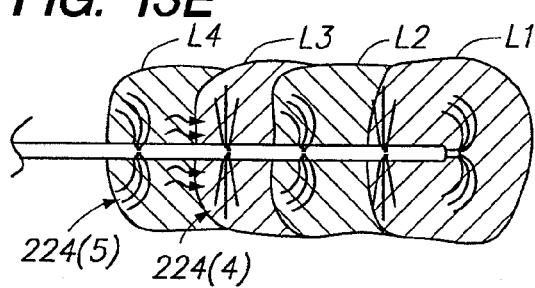

The controller 148 may then operate the switch 150 to decouple the ablation source 146 from the distal active array 224(1) and couple the ablation source 146 to the medial active array 224(3), while continuing to convey RF energy from the ablation source 146. In this manner, RF energy is then conveyed to the medial active array 124(3), which in turn, is transmitted through the tissue to the distal return array 124(2) to create a second lesion portion L2, as illustrated in FIG. 13C. The controller 148 may then unground the distal return array 224(2) and ground the proximal return array 224(4), while continuing to convey RF energy from the ablation source 146. In this manner, RF energy continues to be conveyed to the medial active array 224(3), which in turn, is transmitted through the tissue to the proximal return array 224(4) to create a third lesion portion L3, as illustrated in FIG. 13D. The controller 148 may then decouple the ablation source 146 from the medial active array 224(3) and couple the ablation source 146 to the proximal active array 224(5), while continuing to convey RF energy from the ablation source 146. In this manner, RF energy is then conveyed to the proximal active array 224(5), which in turn, is transmitted through the tissue to the proximal return array 224(4) to create a fourth lesion portion L4, as illustrated in FIG. 13E.

As previously described with respect to the electrode arrays 124, the electrode arrays 224 may be configured in another bipolar arrangement by conveying RF current from the electrode arrays 224(2) and 224(4) to the electrode arrays 224(1), 224(3), and 224(5). In this case, the electrode arrays 224(1), 224(3), and 224(5) will serve as distal, medial, and proximal return arrays, and the electrode arrays 224(2) and 224(4) will serve as distal and proximal active arrays.

Figure 14A:
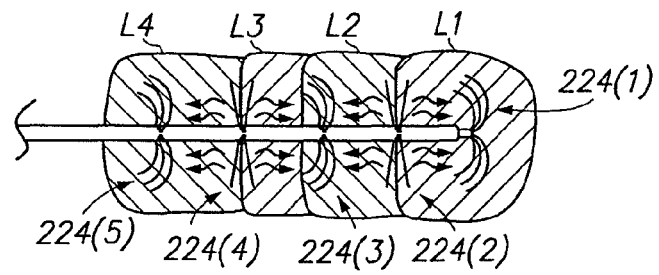
FIGS. 14A-14E are cross-sectional views of two different bipolar arrangements of the probe assembly of FIG. 12, particularly showing the use of distal and proximal active electrode arrays, and distal, medial, and proximal return electrode arrays.

For example, the RF generator 104 may be configured to simultaneously convey RF energy from the active electrode arrays 224(2) and 224(4) to the return electrode arrays 224(1), 224(3), and 224(5). This can be accomplished by the controller 148, which can operate the switch 150 to couple the ablation source 146 to the active arrays 224(2) and 224(4), while the return arrays 224(1), 224(3), and 224(5) are grounded. Thus, RF energy is conveyed from the distal active array 224(2), through the tissue, to the distal return array 224(1) to create a first lesion portion L1, from the distal active array 224(2), through the tissue, to the medial return array 224(3) to create a second lesion portion L2, from the proximal active array 224(4), through the tissue, to the medial return array 224(3) to create a third lesion portion L3, and from the proximal active array 224(4), through the tissue, to the proximal return array 224(5) to create a fourth lesion portion L4 (FIG. 14A). The composite of the lesion portions L1-L4 forms the lesion L.

Figure 14B:
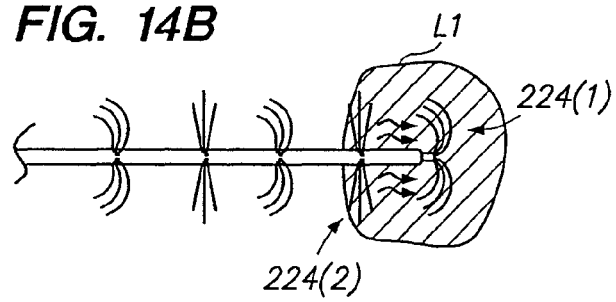
Figure 14C:
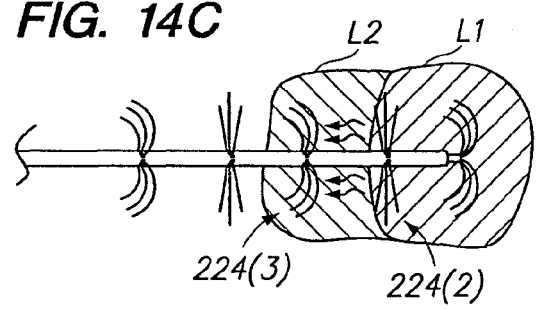

Alternatively, the RF generator 104 may be configured to sequentially convey RF energy from the active electrode arrays 224(2) and 224(4) to the return electrode arrays 224(1), 224(3), and 224(5). In particular, with the ablation source 146 decoupled from the proximal active array 224(4), and the proximal and medial return arrays 224(2) and 224(4) grounded, the controller 148 may operate the switch 150 to first couple the ablation source 150 to the distal active array 224(2), while conveying RF energy from the ablation source 150. In this manner, RF energy is conveyed to the distal active array 224(2), which in turn, is transmitted through the tissue to the distal return array 224(1) to create a first lesion portion L1, as illustrated in FIG. 14B. The controller 148 may then unground the distal return array 224(1) and ground the medial return array 224(3), while continuing to convey RF energy from the ablation source 146. In this manner, RF energy continues to be conveyed to the distal active array 224(2), which in turn, is transmitted through the tissue to the medial return array 124(3) to create a second lesion portion L2, as illustrated in FIG. 14C.

Figure 14D:
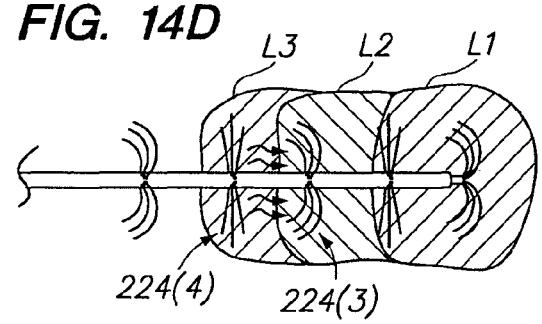
Figure 14E:
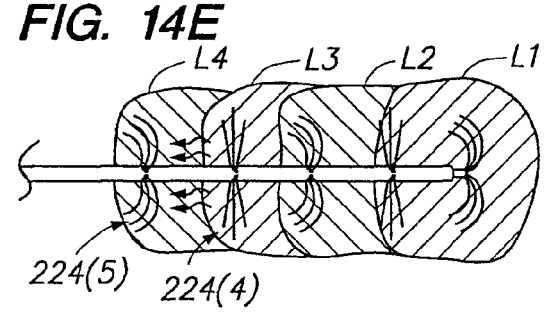

The controller may then decouple the ablation source 146 from the distal active array 224(2) and couple the ablation source 146 to the proximal active array 224(4), while continuing to convey RF energy from the ablation source 146. In this manner, RF energy is then conveyed to the proximal active array 224(4), which in turn, is transmitted through the tissue to the medial return array 224(3) to create a third lesion portion L3, as illustrated in FIG. 14D. The controller may then unground the medial return array 224(3) and ground the proximal return array 224(5), while continuing to convey RF energy from the ablation source 146. In this manner, RF energy continues to be conveyed from the proximal active array 224(4), which in turn, is transmitted through the tissue to the proximal return array 224(5) to create a fourth lesion portion L4, as illustrated in FIG. 14E.

Figure 15:
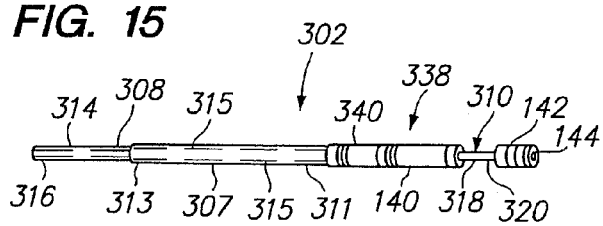
FIG. 15 is a perspective view of still another ablation probe assembly that can alternatively be used in the tissue treatment system of FIG. 1, wherein the probe assembly is particularly shown in its retracted state.
Figure 16:
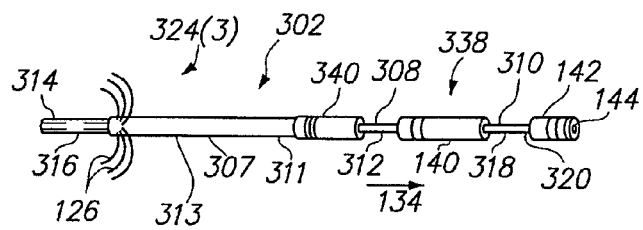
FIG. 16 is a perspective view of the probe assembly of FIG. 15, wherein the probe assembly is particularly shown in its partially deployed state.
Figure 17:
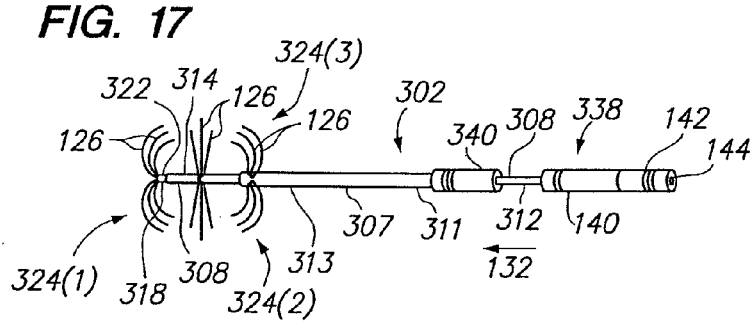
FIG. 17 is a perspective view of the probe assembly of FIG. 15, wherein the probe assembly is particularly shown in its fully deployed state.

Referring now to FIGS. 15-17, another probe assembly 302 that can be used in the treatment system 100 will now be described. The probe assembly 302 is similar to the previously described probe assembly 102, with the exception that the probe assembly 302 deploys the active electrode arrays in opposite directions. In particular, the probe assembly 302 generally comprises an outer cannula 307, an inner cannula 308 slidably disposed within the cannula 307, and an inner probe 310 slidably disposed within the inner cannula 308. The outer cannula 307 has a proximal end 311, a distal end 313, and a central lumen 315 (shown in phantom in FIG. 15) extending through the outer cannula 307. The inner cannula 308 has a proximal end 312, a distal end 314, and a central lumen 316 (shown in phantom in FIGS. 15 and 16) extending through the cannula 308. The outer cannula 307 and inner cannula 308 may be composed of the same material and have the similar dimensions as the previously described cannula 108, with the caveat that the outer cannula 307 is somewhat shorter than the inner cannula 308.

The inner probe 310 comprises a reciprocating shaft 318 having a proximal end 320 and a distal end 322, and two axially aligned electrode arrays 324(1) and 324(2), each of which comprises a plurality of tissue penetrating needle electrodes 126 suitably mounted to the distal end 322 of the inner probe shaft 318. An additional electrode array 324(3) is mounted to the distal end 314 of the inner cannula 308. The three electrode arrays 324 are configured into two bipolar electrode pairs, with the electrode array 324(2) being common to the electrode pairs. That is, a first electrode pair is formed by the electrode arrays 324(1) and 324(2), and a second electrode pair formed by the electrode arrays 324(3) and 324(2). The electrode array 324(2) has a polarization that is opposite to the polarization of the electrode arrays 324(1) and 324(3). In the illustrated embodiment, the electrode arrays 324(1) and 324(3) are configured as distal and proximal active arrays, and the electrode array 324(2) is configured as a return array.

It can be appreciated that longitudinal translation of the inner probe shaft 318 relative to the inner cannula 308 in the distal direction 132 deploys the electrode arrays 324(1) and 324(2) from the distal end 314 of the inner cannula 308 (FIG.

17), and longitudinal translation of the inner probe shaft 318 relative to the inner cannula 308 in the proximal direction 134 retracts the electrode arrays 324(1) and 324(2) into the distal end 314 of the inner cannula 308 (FIG. 15). The inner cannula 308 comprises a distal opening (not shown) in which the cannula lumen 316 terminates, and circumferentially disposed ports (not shown) that extend through the wall of the inner cannula 308. The needle electrodes 126 of the distal active array 324(1) deploy out from the distal opening, and the needle electrodes 126 of the return array 324(2) deploy out from the distal ports.

Longitudinal translation of the inner cannula 308 relative to the outer cannula 307 in the proximal direction 132 deploys the proximal active electrode array 324(3) from the distal end 314 of the outer cannula 307 (FIG. 16), and longitudinal translation of the inner cannula 308 relative to the outer cannula 307 in the distal direction 134 retracts the proximal active electrode array 324(3) into the distal end 313 of the outer cannula 307 (FIG. 15). The outer cannula 307 comprises circumferentially disposed ports (not shown) that extend through the wall of the outer cannula 307. The needle electrodes 126 of the proximal active array 324(3) deploy out from the distal ports.

As can be seen in FIG. 17, the geometry of the deployed electrode arrays 324(1), 324(2), and 324(3) are the same as the geometry of the deployed electrode arrays 124(1), 124(2), and 124(3), respectively, with the exception that the needle electrodes 126 of the proximal active array 324(3) evert distally, so that they face partially or fully in the distal direction 132 when fully deployed. The probe assembly 302 further comprises a connector assembly 338, which is similar to the previously described connector assembly 138, with the exception that it includes an additional connector sleeve 340 mounted to the proximal end 311 of the outer cannula 307.

In order to provide a more efficient ablation process, RF current can be delivered to the electrode arrays 324 in a bipolar fashion in the same manner as RF current is delivered to the respective electrode arrays 124 described above. The only difference is that, if desired, RF current may be delivered to the electrode array 324(3) via the electrically conductive inner cannula 308, rather than the inner probe shaft 318.

Figure 18A:
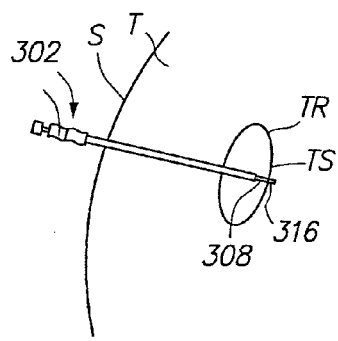
FIGS. 18A-18C are cross-sectional views of one preferred method of using the tissue ablation system of FIG. 4, with the alternative probe assembly of FIG. 15, to treat tissue.

Referring now to FIGS. 18A-18D, the operation of the probe assembly 302 in treating a treatment region TR within tissue T located beneath the skin or an organ surface S of a patient. The operation of the probe assembly 302 is similar to that of the probe assembly 102, with the exception that the deployment process differs. In particular, the probe assembly 302, while fully retracted, is first introduced within the treatment region TR, so that the distal end 316 of the inner cannula 308 is located at the target site TS, as shown in FIG. 18A. This can be accomplished in the same manner as the previously described probe assembly 302.

Figure 18B:
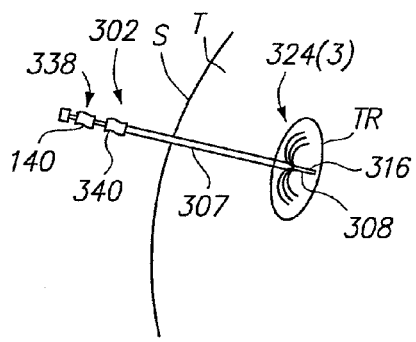

After the probe assembly 302 is properly placed, the connector sleeve 140 of the connector assembly 338 is pulled proximally relative to the connector sleeve 138, thereby proximally displacing the inner cannula 308 relative to the outer cannula 307. As a result, the proximal active electrode array 324(3) is deployed radially outward from the distal openings within the outer cannula 307, as shown in FIG. 18B. Notably, the distal end 316 of the inner cannula 308 is proximally displaced within the treatment region TR. Thus, the target site TS will generally be located distal to the treatment region TR, so that when the distal end 316 of the inner cannula 308 will reside within the treatment region TR when the proximal active electrode array 324(3) is deployed.

Figure 18C:
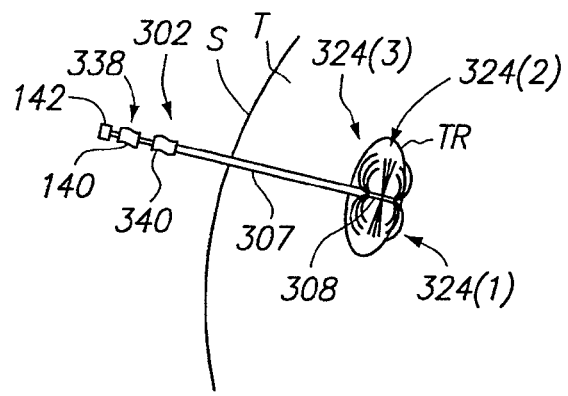

Next, the connector member 142 is pushed distally relative to the connector sleeve 140, thereby distally displacing the inner probe shaft 318 relative to the inner cannula 308. As a result, the distal active electrode array 324(1) is deployed radially outward from the distal opening of the inner cannula 308, and the return electrode array 324(2) is deployed radially outward from the distal openings within the inner cannula 308, as shown in FIG. 18C. The RF generator 104 is then connected to the connector assembly 138 via the electrical connector 144 and then operated to create a three-dimensional lesion L within the treatment region TR similar to that illustrated in FIG. 9D. The difference is that there will generally be more symmetry in the lesion created by the probe assembly 302, since the oppositely everted active electrode arrays 324(1) and 324(3) will be geometrically symmetrical about the planar return electrode array 324(2).

In the preferred embodiment, RF current is simultaneously conveyed from the distal and proximal active electrode arrays 324(1) and 324(3) to the return electrode array 324(2). This can be accomplished in the same manner previously described above with respect to FIG. 10A. Alternatively, RF current can be sequentially conveyed from the distal and proximal active electrode arrays 324(1) and 324(3) to the return electrode array 324(2). This can be accomplished in the same manner previously described above with respect to FIGS. 10B and 10C. Or the electrode arrays 324(1) and 324(3) can be operated as return arrays, and the electrode array 324(2) can be operated as an active array, in which case, RF current can be simultaneously or sequentially delivered from the active electrode array 324(2) to the return electrode arrays 324(1) and 324(3). This can be accomplished in the same manner previously described above with respect to FIG. 11A or FIGS. 11B and 11C, respectively.

Figure 19:
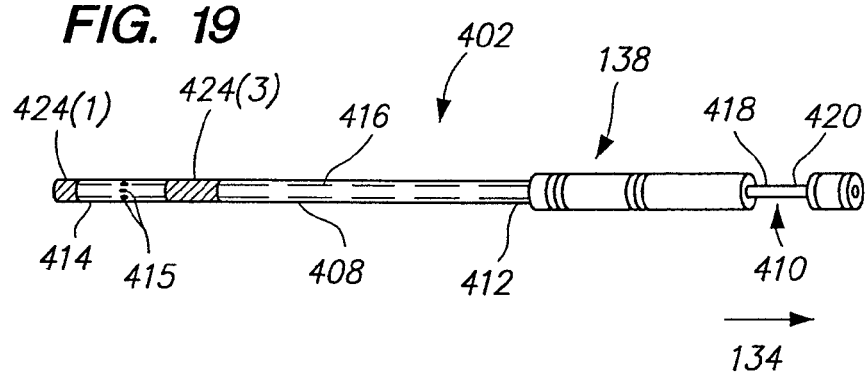
FIG. 19 is a perspective view of still another ablation probe assembly that can alternatively be used in the tissue treatment system of FIG. 1, wherein the probe assembly is particularly shown in its retracted state.
Figure 20:
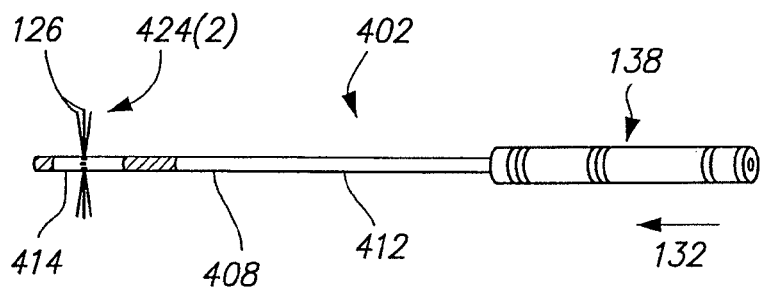
FIG. 20 is a perspective view of the probe assembly of FIG. 19, wherein the probe assembly is particularly shown in its deployed state.

Referring now to FIGS. 19 and 20, another probe assembly 402 that can alternatively be used in the treatment system 100 will now be described. The probe assembly 402 is similar to the previously described probe assembly 102, with the exception that the active electrode elements of the probe assembly 402 are ring electrodes, rather than electrode arrays. In particular, the probe assembly 402 generally comprises a cannula 408 and an inner probe 410 slidably disposed within the cannula 408. The cannula 408 has a proximal end 412, a distal end 414, and a central lumen 416 (shown in phantom in FIG. 19) extending through the cannula 408.

The inner probe 410 comprises a reciprocating shaft 418 having a proximal end 420 and a distal end 422, and an electrode array 424(2), which comprises a plurality of tissue penetrating needle electrodes 126 suitably mounted to the distal end 422 of the inner probe shaft 418. The cannula 408 comprises two axially aligned ring electrodes 424(1) and 424(3) disposed along the shaft of the cannula 408. The ring electrodes 424(1) can be formed on the cannula 408 in any one of a variety of ways. In the illustrated embodiment, the cannula 408, itself, is electrically conductive, so that annular portions of the cannula 408 can form the ring electrodes 424(1) and 424(3). The lengthwise portions of the cannula 408 between the ring electrodes 424(1) and 424(3) are covered within an insulative material in order to concentrate the ablation energy at the ring electrodes 424(1) and 424(3). Alternatively, the ring electrodes 424(1) and 424(3) can be discrete electrically conductive rings that are circumferentially mounted around the cannula 408. In this case, electrically conductors (not shown) can be mounted to the ring electrodes 424(1) and 424(3) routed back through the cannula lumen 416 to the proximal end 412. The cannula 408 can either be composed of, or covered with, an insulative material, so that the ablation energy can be focused at the ring electrodes 424(1) and 424(3). Optionally, a portion of the needle electrodes 126 of the return array 424(2) can be coated with an insulative material (not shown), with the distal ends of the needle electrodes 126 exposed. In this manner, the resulting lesion that is generated by the probe assembly 102 can be shaped. For example, the ablation energy can be focused at the distal tips of the needle electrodes 126 in order to provide greater lesion coverage.

The three electrode arrays 424 are configured into two bipolar electrode pairs, with the electrode array 424(2) being common to the electrode pairs. That is, a first electrode pair is formed by the electrode arrays 424(1) and 424(2), and a second electrode pair is formed by the electrode arrays 424(3) and 424(2). The electrode array 424(2) has a polarization that is opposite to the polarization of the ring electrodes 424(1) and 424(3). In the illustrated embodiment, the ring electrodes 424(1) and 424(3) are configured as distal and proximal active elements, and the electrode array 424(2) is configured as a return array. Alternatively, the ring electrodes 424(1) and 424(3) can be configured as distal and proximal return elements, and the electrode array 424(2) configured as an active array.

It can be appreciated that longitudinal translation of the inner probe shaft 418 relative to the inner cannula 408 in the distal direction 132 deploys the electrode array 424(2) from the distal end 414 of the inner cannula 408 (FIG. 20), and longitudinal translation of the inner probe shaft 318 relative to the inner cannula 308 in the proximal direction 134 retracts the electrode array 424(2) into the distal end 414 of the cannula 408 (FIG. 19). The cannula 408 comprises circumferentially disposed ports 139 that extend through the wall of the cannula 408. The needle electrodes 126 of the return array 424(2) deploy out from the distal ports 139. As can be seen in FIG. 20, the geometry of the deployed electrode arrays 424(2) is the same as the geometry of the deployed electrode arrays 124(2).

Figure 21:
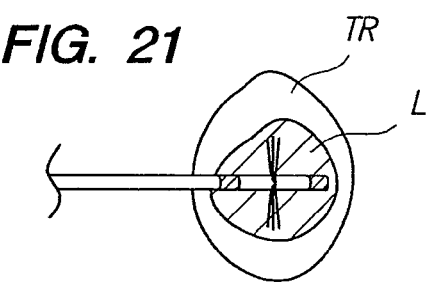
FIG. 21 is a cross-section view of a bipolar arrangement of the probe assembly of FIG. 19 being operated to treat tissue.

In order to provide a more efficient ablation process, RF current can be delivered to the electrode arrays 424 in a bipolar fashion in the same manner as RF current is delivered to the respective electrode arrays 124 described above. Operation of the probe assembly 402 is similar to the operation of the probe assembly 102 described with respect to FIGS. 9A-9D, with the exception that a diamond shaped lesion L is generated within the treatment region TR, as illustrated in FIG. 21.

It should be noted that although single ablation probes have been previously described as being used to perform tissue ablation, multiple probes can also be used. For example, first and second electrode arrays may be mounted on first probe, and a third electrode array mounted on a second probe. Prior to performing the actual tissue ablation, the probes can be introduced into the tissue, such that the third electrode array is distal to and axially aligned with the first and second electrode arrays. Thus, first and second electrode arrays on the first probe may be characterized as proximal and medial electrode arrays, and the third electrode array on the second probe may be characterized as a distal electrode array. Alternatively, the probes can be introduced into the tissue, such that the third electrode array is proximal to and axially aligned with the first and second electrode arrays. Thus, first and second electrode arrays on the first probe may be characterized as medial and distal electrode arrays, and the third electrode array on the second probe may be characterized as a proximal electrode array. Even more alternatively, the probes can be introduced into the tissue, such that the third electrode array is between and axially aligned with the first and second electrode arrays. In this case, the first and second electrode arrays on the first probe may be characterized as proximal and distal electrode arrays, and the third electrode array on the second probe may be characterized as a medial electrode array. In each of the above cases, the electrode arrays should be arranged, such that they are axially aligned with each other, and such that the proximal and distal electrode arrays are oppositely polarized from the medial electrode array. The importance is that the electrode arrays be axially arranged, and that the arrangement allows ablation energy to be delivered between the medial electrode array and the respective proximal and distal electrode arrays.

Although all of the ablation processes described above use a stabilized electrode array arrangement throughout the treatment process, thereby simplifying and reducing the procedure time, the electrode array arrangement may be made more dynamic to provide for improved lesions. For example, if two ablation probes are used, a medial electrode array located on a second probe can be moved closer to the distal electrode array on the first probe when ablating therebetween, and then can be moved closer to the proximal electrode array on the first probe when ablating therebetween. As a result, the distance between the pertinent electrode arrays at any given time can be reduced, thereby maximizing the efficiency of the ablation process. The same result can be achieved using a single ablation probe by making the medial array movable along the axis of the probe, so that it can be distally moved to be placed closer to the distal electrode array when ablating therebetween, and proximal moved to be placed closer to the proximal electrode array when ablating therebetween. Thus, it can be appreciated that the use of dynamically movable electrode arrays may add more complexity to the process, but may provide or a more efficient and effective lesion.

It should also be noted that although the characterization of any given electrode array has been previously described as being either as an active array or a return array, a given electrode array may be configured such that it can be dynamically selected to be either an active array or a return array. For example, in a three-electrode array arrangement, the distal electrode array can be configured as an active electrode array, and the medial electrode array can be configured as a return electrode array to provide a first ablation region therebetween. The medial electrode array can then be configured as an active electrode array and the proximal electrode array can be configured as a return electrode array to provide a second ablation region therebetween.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A tissue ablation system comprising:
   a medical probe assembly for ablating tissue comprising:
   a substantially rigid elongated member having a distal end;
   first and second of electrode elements mechanically coupled to the distal end of the substantially rigid elongated member, wherein the second electrode element is located proximal to the first electrode element;
   a third electrode element mechanically coupled to the substantially rigid elongated member at a location between the first and second electrode elements, the third electrode element having a planar configuration arranged generally orthogonal to a long axis of the substantially rigid elongated member;

a radiofrequency generator comprising:
   a radiofrequency ablation source; and
   a controller operatively coupled to a switch and configured to selectively couple at least one of the first and second electrode elements or the third electrode element to the radiofrequency ablation source and selectively couple at least one of the remaining electrode elements to ground.

2. The system of claim 1, wherein the controller is configured to selectively couple the first and second electrode elements to the radiofrequency ablation source and the third electrode element to ground.

3. The system of claim 2, wherein the controller is configured to sequentially provide radiofrequency energy from the first and second electrode elements to the third electrode element.

4. The system of claim 2, wherein the controller is configured to simultaneously provide radiofrequency energy from the first and second electrode elements to the third electrode element.

5. The system of claim 1, wherein the controller is configured to selectively couple one of the first and second electrode elements and the third electrode element to the radiofrequency ablation source and the remaining electrode element of the first and second electrode elements to ground.

6. The system of claim 1, wherein the controller is configured to selectively couple one of the first and second electrode elements to the radiofrequency ablation source and the remaining electrode elements to ground.

7. The system of claim 1, wherein the controller is configured to selectively couple the third electrode element to the radiofrequency ablation source and the remaining electrode elements to ground.

8. The system of claim 7, wherein the controller is configured to sequentially provide radiofrequency energy from the third electrode element to the first and second electrode elements.

9. The system of claim 7, wherein the controller is configured to simultaneously provide radiofrequency energy from the third electrode element to the first and second electrode elements.

10. The system of claim 1, wherein the first and second electrode elements and the third electrode element each comprise a plurality of electrodes that radially extend from the elongate member.

11. The system of claim 10, wherein the first and second electrode elements assume an outwardly curved shape when deployed.

12. The system of claim 1, wherein the elongate member comprises an inner shaft slidably disposed within a cannula having a lumen.

13. The system of claim 1, wherein the first and second electrode elements are oriented in opposite direction in a deployed state.

14. A tissue ablation system comprising:
   a medical probe assembly for ablating tissue comprising:
      a substantially rigid elongated member having a distal end;
      at least three electrode elements mechanically coupled to the distal end of the substantially rigid elongated member, wherein at least two non-adjacent electrode elements of the at least three electrode elements are axially separated from one another along the substantially rigid elongated member and have a polarization that is opposite the polarization of the remaining electrode element(s) interposed axially between at least two non-adjacent electrode elements;
   a radiofrequency generator comprising:
      a radiofrequency ablation source; and
      a controller operatively coupled to a switch and configured to selectively couple at least one of at least two non-adjacent electrode elements to the radiofrequency ablation source and selectively couple the remaining electrode element(s) to ground.

15. The system of claim 14, wherein the at least three electrode elements comprise first, second, third, fourth, and fifth electrode elements and wherein the second and fourth electrode elements have a polarization that is opposite to that of the first, third, and fifth electrode elements.

16. The system of claim 15, wherein the controller is configured to selectively couple at least one of the first, third, and fifth electrode elements to the radiofrequency ablation source and selectively couple at least one of the second and fourth electrode elements to ground.

17. The system of claim 16, wherein the medical probe assembly comprises four ablation zones disposed between adjacent electrode elements and wherein the controller is configured to sequentially provide radiofrequency energy to each of the four ablation zones.

18. The system of claim 16, wherein the medical probe assembly comprises four ablation zones disposed between adjacent electrode elements and wherein the controller is configured to simultaneously provide radiofrequency energy to each of the four ablation zones.

* * * * *